United States Patent [19]

Kornberg et al.

[11] Patent Number: 5,353,804
[45] Date of Patent: Oct. 11, 1994

[54] METHOD AND DEVICE FOR PERCUTANEOUS EXISIONAL BREAST BIOPSY

[75] Inventors: Elliot Kornberg, Cocoa Beach, Fla.; William R. Tarello, Bethesda, Md.

[73] Assignee: PEB Biopsy Corporation, Cocoa Beach, Fla.

[21] Appl. No.: 33,785

[22] Filed: Mar. 17, 1993

Related U.S. Application Data

[63] Continuation of Ser. No. 880,208, May 8, 1992, Pat. No. 5,197,484, which is a continuation-in-part of Ser. No. 584,614, Sep. 18, 1990, Pat. No. 5,111,828.

[51] Int. Cl.$^5$ ............................................. A61B 10/00
[52] U.S. Cl. ................................................ 128/754
[58] Field of Search ....................... 128/749, 751–754; 606/167, 170, 171

[56] References Cited

U.S. PATENT DOCUMENTS

| | | |
|---|---|---|
| RE 33,258 | 7/1990 | Onik et al. |
| D. 303,290 | 9/1989 | McMenamy et al. |
| 1,275,669 | 8/1918 | Forbes . |
| 2,541,542 | 2/1951 | Perez et al. ............. 128/754 |
| 3,087,486 | 4/1963 | Kilpatrick . |
| 3,470,867 | 11/1964 | Goldsmith . |
| 3,477,423 | 1/1967 | Griffith . |
| 3,516,412 | 6/1970 | Ackerman . |
| 3,547,121 | 12/1970 | Cherry . |
| 3,583,390 | 6/1971 | Jascalevich . |
| 3,587,560 | 6/1971 | Glassman . |
| 3,605,721 | 11/1969 | Hallac . |
| 3,628,524 | 12/1971 | Jamshidi . |
| 3,674,950 | 7/1972 | Scoville . |
| 3,836,776 | 9/1974 | Gullekson . |
| 3,902,501 | 9/1975 | Citron et al. |
| 3,929,123 | 12/1975 | Jamshidi . |
| 4,007,732 | 2/1977 | Kravle et al. ............. 128/754 |
| 4,099,518 | 7/1978 | Baylis et al. |
| 4,177,797 | 12/1979 | Baylis et al. ............. 128/754 |
| 4,243,048 | 1/1981 | Griffin . |
| 4,249,541 | 2/1981 | Pratt . |
| 4,306,570 | 12/1981 | Matthews . |
| 4,485,815 | 12/1984 | Amplatz et al. |
| 4,532,935 | 8/1985 | Wang . |
| 4,586,926 | 5/1986 | Osborne . |
| 4,597,385 | 7/1986 | Watson . |
| 4,651,752 | 3/1987 | Fuerst ....................... 128/754 |

(List continued on next page.)

FOREIGN PATENT DOCUMENTS

2610508 8/1988 France .

OTHER PUBLICATIONS

Bishop, Jerry E. "New Biopsy Technique for Breast Lumps is Called Quicker, Cheaper, Less Painful" *The Wall Street Journal*, Feb. 5, 1992: B1.

Lowen, Sara. "Breast Anxiety", *The Baltimore Magazine*, Apr. 1992, pp. 27–31.

(List continued on next page.)

*Primary Examiner*—Max Hindenburg
*Attorney, Agent, or Firm*—Beveridge, DeGrandi, Weilacher & Young

[57] ABSTRACT

An apparatus for removing suspect breast tissue which includes a penetrating member in the form of a stylet with a tapered front end that can be guided along a localization guide wire. The apparatus also including a first cutting device in the form of a cannula slidingly engaged with the stylet. A driving assembly is in driving engagement with the cannula and, upon activation, potential energy stored in the driving assembly acts to drive the forward end of the cannula forward of the stylet's forward end so as to define a core cavity. A second cutting device which includes a garret wire having a looped section positioned within a recess at the forward end of the cannula is also provided. The driving assembly preferably also acts to rotate the cannula with a cam arrangement such that the cannula rotates when being driven forward. The garret wire is also attached to the rotating cannula such that the wire is drawn up to a stop bead just at the time the cannula reaches its maximum forward extension and further rotation of the cannula results in the contraction of the wire loop and a cutting of a core sample of suspect breast tissue.

21 Claims, 10 Drawing Sheets

U.S. PATENT DOCUMENTS

| | | |
|---|---|---|
| 4,655,226 | 4/1987 | Lee . |
| 4,667,684 | 5/1987 | Leigh . |
| 4,678,459 | 7/1987 | Onick et al. . |
| 4,682,606 | 7/1987 | DeCaprio ............................ 128/754 |
| 4,691,333 | 9/1987 | Gabriele et al. . |
| 4,696,308 | 9/1987 | Meller et al. ........................ 128/754 |
| 4,708,147 | 11/1987 | Haaga . |
| 4,727,565 | 2/1988 | Ericson . |
| 4,766,906 | 8/1988 | Wang . |
| 4,776,346 | 10/1988 | Beraha et al. . |
| 4,784,134 | 11/1988 | Arana . |
| 4,790,329 | 12/1988 | Simon . |
| 4,793,363 | 12/1988 | Ausherman et al. . |
| 4,799,494 | 1/1989 | Wang . |
| 4,817,631 | 4/1989 | Schnepp-Pesch et al. . |
| 4,832,044 | 5/1989 | Garg . |
| 4,838,280 | 6/1989 | Haaga . |
| 4,841,967 | 6/1989 | Chang et al. . |
| 4,850,373 | 7/1989 | Zatloukal et al. . |
| 4,881,550 | 11/1989 | Kothe . |
| 4,893,635 | 1/1990 | Poirier . |
| 4,917,100 | 4/1990 | Nottke . |
| 4,919,146 | 4/1990 | Rhinehart et al. . |
| 4,926,877 | 5/1990 | Bookwalter ......................... 128/754 |
| 4,935,025 | 6/1990 | Bundy et al. . |
| 4,940,061 | 7/1990 | Terwilliger et al. . |
| 4,966,583 | 10/1990 | Debbas . |
| 4,971,067 | 11/1990 | Boldue et al. . |
| 4,976,723 | 12/1990 | Schad . |
| 4,989,614 | 2/1991 | Dejter et al. . |
| 4,991,592 | 2/1991 | Christ . |
| 5,056,529 | 10/1991 | De Groot . |
| 5,125,413 | 6/1992 | Baran . |
| 5,127,419 | 7/1992 | Kaldany . |
| 5,133,121 | 7/1992 | Kedem . |
| 5,197,484 | 3/1993 | Kornberg et al. .................. 128/754 |

OTHER PUBLICATIONS

Diseases, edited by J. R. Harris, S. Hellman, I. C. Henderson, and D. W. Kinne, 1987, pp. 77–84.

National-Standard Medical Products, Pamphlet—Suggested Procedure: Hawkins Breast Localization Needle III Sep. 1990.

Fischer Imaging Corp. Brochure—"Advanced Mammo-Biopsy system—the alternative to surgical biopsy" 1989.

Wolmark, N., "2. Biopsy as a Prelude to Definitive Operative Therapy for Breast Cancer", *Manual of Oncologic Therapeutics,* 1989, pp. 8–11.

Micklos, T. J., "13. Percutaneous Biopsy Techniques", *Manual of Oncologic Therapeutics,* edited by R. E. Wittes, 1989, pp. 39–42.

Haagensen, C. D., et al., *Breast Carcinoma Risk and Detection,* 1981, Chapter 26, pp. 516–525.

Wilson, R. E., "3. History and Physical Diagnosis of Breast Carcinoma", In *Carcinoma of the Breast: Diagnosis and Treatment,* 1983, pp. 49 & 56–58.

Bragg, D. G. et al., "Radiologic Techniques in Cancer", Cancer Principles & Practice of Oncology, edited by V. T. DeVita, Jr., S. Hellman, and S. A. Rosenberg, Third Edition, 1989, pp. 440, 446–448 and 462.

Miller, D. L., et al., "Interventional Radiology in Oncology", Cancer Principles & Practice of Oncology, edited by V. T. DeVita, Jr, S. Hellman and S. A. Rosenberg, Third Edition, 1989, pp. 464–466 and 475–476.

Spratt, J. S., et al., "Surgical Management", Cancer of the Breast, edited by Donegan and Spratt, 1988, Chapter 13, pp. 403–407 and 459–461.

Annonier, C., Female Breast Examination, 1986, pp. 89–90.

Donegan, W. L., "Diagnosis", Cancer of the Breast, edited by W. L. Donegan and J. S. Spratt, 1988, Chapter 6, pp. 125, 157–158 and 162–166.

Kinne, D. W. et al., "Physical Examination and Mammography in the Diagnosis of Breast Disease", Breast

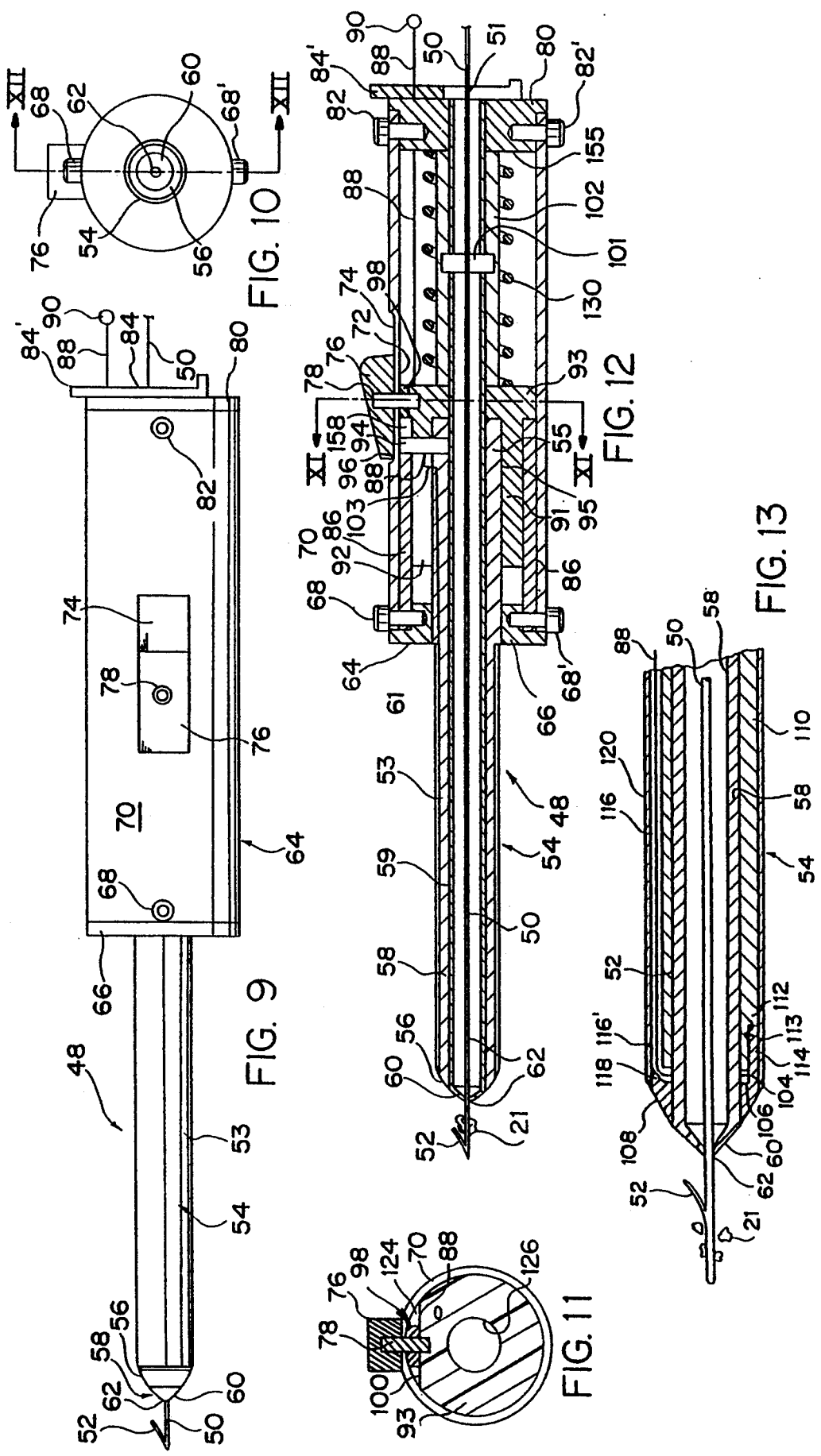

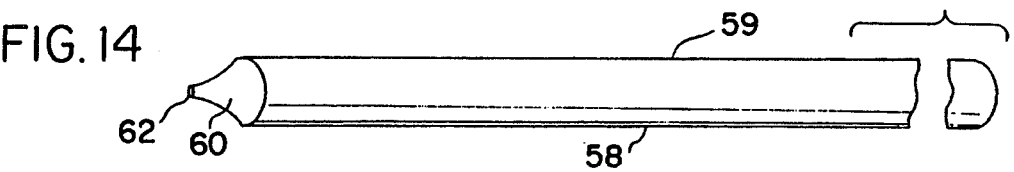
FIG.14
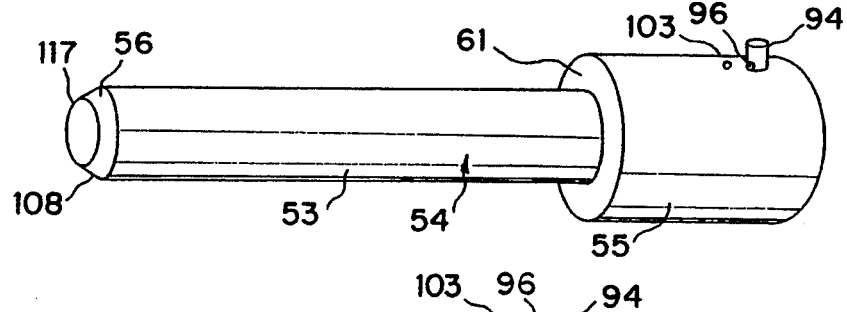
FIG.15
FIG.16
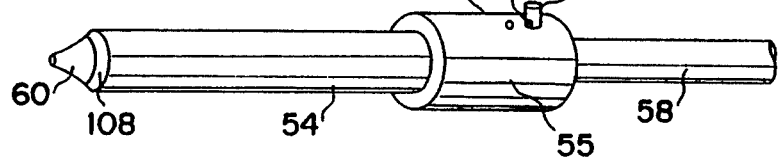
FIG.17
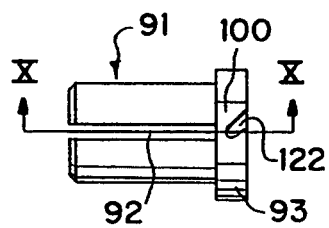 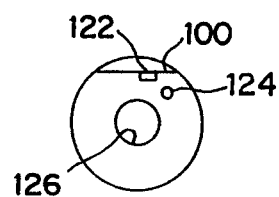 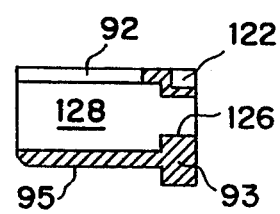
FIG.18  FIG.19  FIG.20
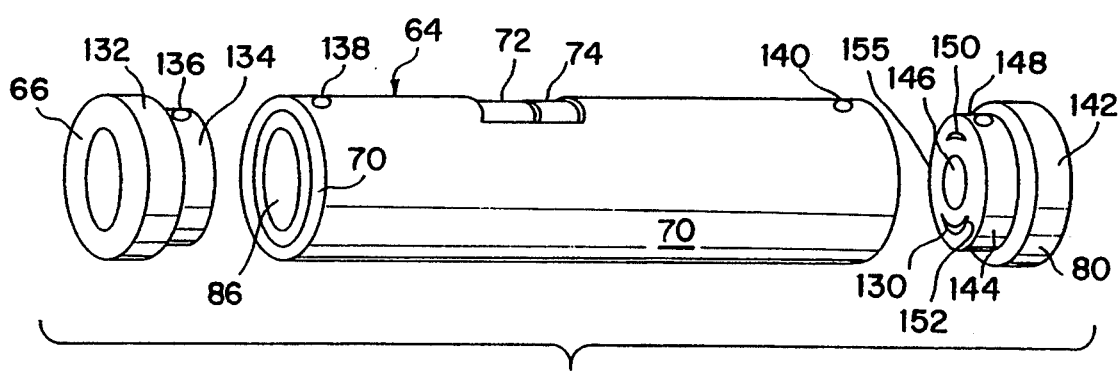
FIG.21

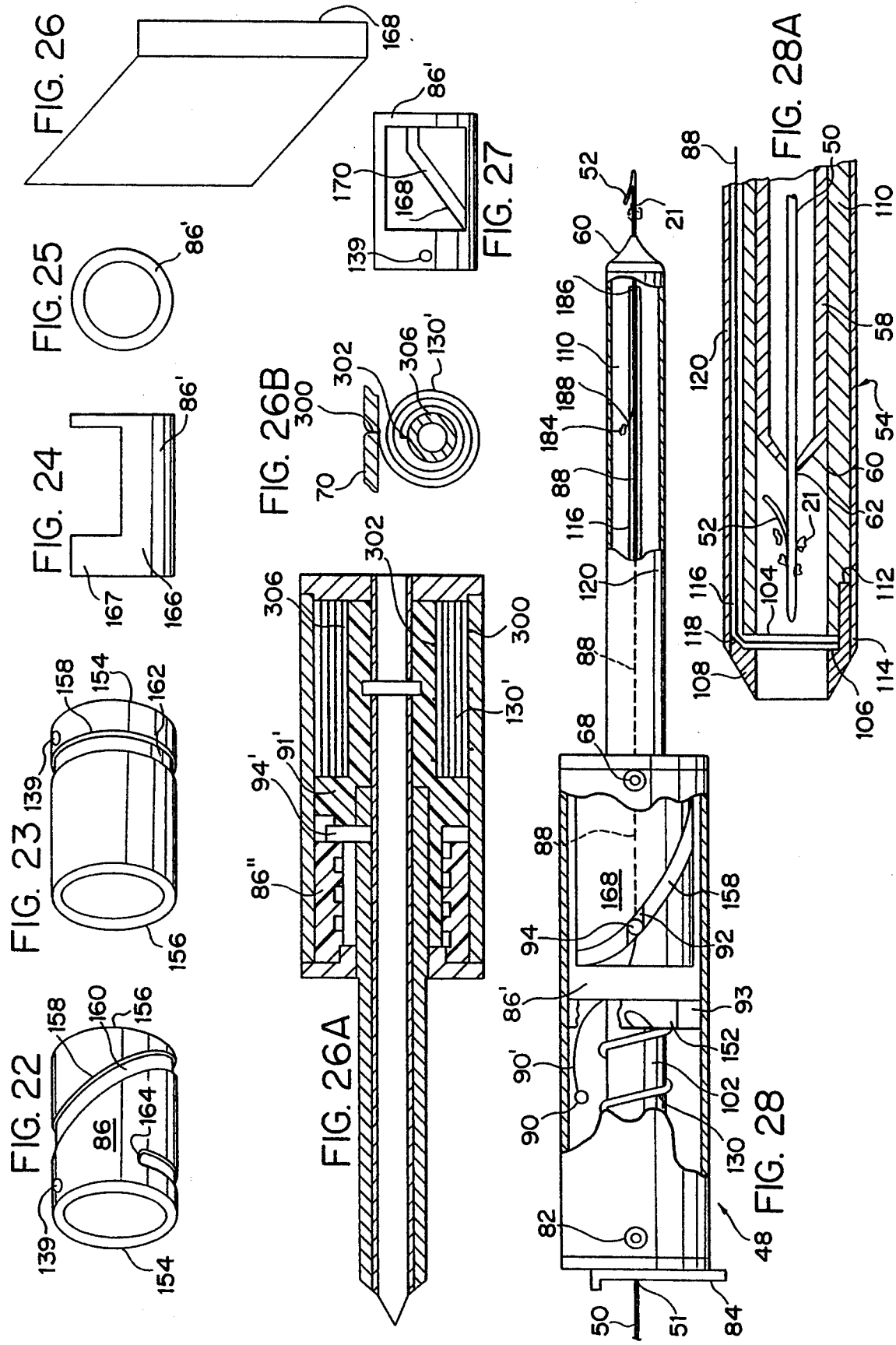

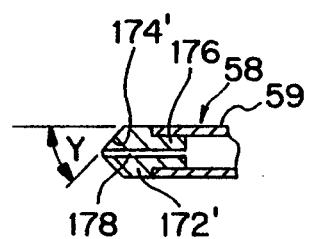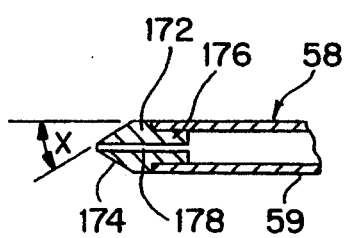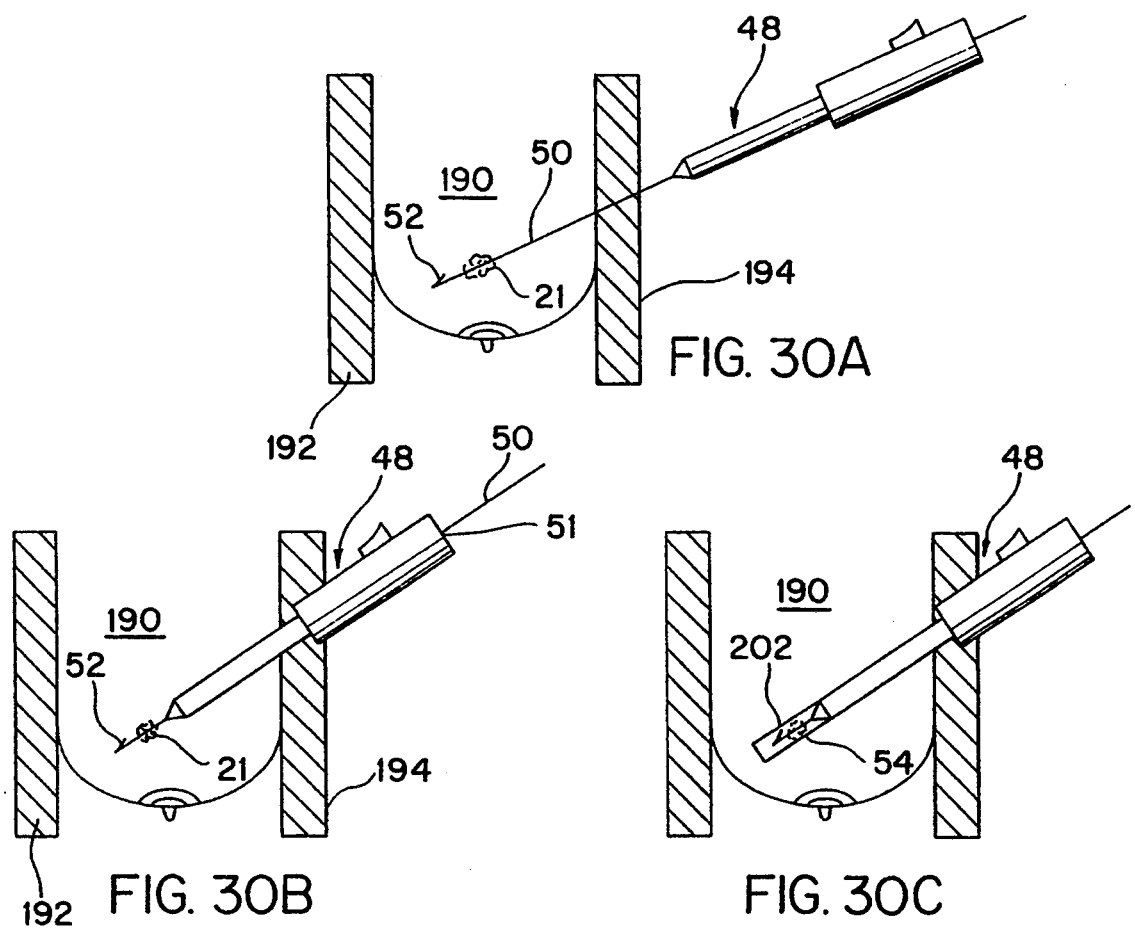

METHOD AND DEVICE FOR PERCUTANEOUS EXISIONAL BREAST BIOPSY

The present application is a continuation of U.S. Ser. No. 07/880,208 filed on May 8, 1992 and now U.S. Pat. No. 5,197,484, which is a continuation-in-part application of U.S. Ser. No. 07/584,614 filed on Sep. 18, 1990 and now U.S. Pat. No. 5,111,828.

BACKGROUND OF THE INVENTION

The present invention concerns a method and apparatus for percutaneous excisional breast biopsy and a percutaneous excisional breast biopsy device (PEBB device).

Currently, there is great emphasis on early diagnosis of breast cancer through the use of mammography since early intervention may substantially alter the course of the disease. Mammography is capable of detecting very small abnormalities, often nonpalpable, within the breast. However, mammography is usually unable to differentiate between malignant and benign lesions. Thus, the surgeon is confronted with the problem of biopsying these lesions.

The only method of making a definitive diagnosis of breast cancer is by histologic examination of the suspect tissue. There are essentially two techniques for obtaining a histologic diagnosis: open surgery biopsy and needle biopsy.

In surgical biopsy the suspect tissue is removed through a surgical incision. It can be performed under local or general anesthesia, preferably in a surgical suite. Surgical biopsies are either incisional (removal of only a part of the tumor) or excisional (removal of the entire gross tumor or lesion). Small lesions with a diameter about 1 cm or less are usually excised completely. Relative to needle biopsy, surgical biopsy has higher patient morbidity and costs.

A fine needle biopsy involves obtaining cytologic material through aspiration by a syringe and a needle. A cytologist will then examine the cytologic material. Core needle biopsy removes a small core of tissue through the use of various needles designed for this purpose (e.g., Travenol Tru-Cut needle). A pathologist will then remove and examine the suspect tissue. With core needle biopsy a definitive diagnosis is possible only if a positive diagnosis of malignancy is made. The disadvantage of core needle biopsy is that a negative finding is inconclusive because of the possibility of being a false negative. False negatives may be due to an inadequate sample or to the wrong site being sampled. A negative finding usually requires the performance of an open biopsy. Even a positive finding may require surgical excision if conservation therapy is to be employed. The use of needle biopsy is usually restricted to tumors larger than 2 mm in diameter. Needle biopsy of smaller, mobile lesions increases the chances of obtaining a false negative.

The present invention overcomes the disadvantages and shortcomings of the prior art and provides a method and device for percutaneous excisional breast biopsy.

SUMMARY OF THE INVENTION

It is an object of the present invention to provide a percutaneous excisional breast biopsy device (PEBB device) for extracting biopsy samples and for completely removing lesions which are less than 5 mm in diameter with the preferred range being between 2–4 mm.

In one variation, the PEBB device includes: a cannula member having upper proximal and lower distal ends and including a cannula opening at the proximal and distal ends, the cannula has a sharp cutting surface at the distal end; a stylet member having upper proximal and lower distal ends and including a stylet having a pointed distal end capable of spreading tissue, the styler being slidable in the cannula for simultaneous insertion with the cannula, the stylet having a hollow central shaft capable of receiving a localizing needle; and an additional means of cutting tissue.

In another variation, the PEBB device includes: a cannula member having upper proximal and lower distal ends, the cannula has a sharp cutting surface at the distal end; a stylet member or obturator having upper proximal and lower distal ends and a pointed distal end capable of spreading tissue, the stylet being slidable in the cannula for simultaneous insertion with the cannula, the styler having a hollow central shaft capable of receiving a localizing needle; an additional means of cutting tissue; a localizing needle capable of being received into the stylet, the localizing needle capable of receiving a guide wire; a guide wire capable of being received into the localization needle, the guide wire capable of holding position with respect to surrounding tissue.

Various types of localizing needles and guide wires can be used with the PEBB device.

Another object of the present invention is to provide a new method to accurately locate and precisely remove a breast lesion through use of the PEBB device.

In one variation of the method, the following steps are conducted:

(a) locating a breast lesion by mammographic or sonic techniques;

(b) positioning and implanting a localizing needle distal to said breast lesion, said localization needle containing a hooked guide wire;

(c) positioning and implanting said hooked guide wire distal to said breast lesion;

(d) making a small incision on the surface of the breast at the point where said localizing needle enters the breast;

(e) passing a PEBB device over said localizing needle;

(f) inserting said PEBB device through said incision;

(g) further inserting said PEBB device and pushing aside the breast tissue;

(h) positioning said PEBB device to the desired location proximate said lesion;

(i) further inserting into the breast a first cutting surface of said PEBB device to the desired location distal said lesion;

(j) manipulating a second cutting surface of said PEBB device and cutting the portion of the breast tissue distal to said hooked guide wire to separate a portion of said breast tissue containing all of said lesion; and (k) removing the PEBB device containing said lesion.

In another variation of the method, the following steps are conducted after the breast lesion has been located:

(a) positioning and implanting a localizing needle distal to said breast lesion, said localizing needle containing a hooked guide wire;

(b) positioning and implanting said hooked guide wire distal to said breast lesion;

(c) making a small incision on the surface of the breast at the point where said localizing needle enters the breast;

(d) passing a PEBB device over said localizing needle;

(e) inserting said PEBB device through said incision;

(f) further inserting said PEBB device and pushing aside the breast tissue;

(g) positioning said PEBB device to the desired location proximate said lesion;

(h) further inserting into the breast a first cutting surface of said PEBB device to the desired location near said lesion;

(i) manipulating a second cutting surface of said PEBB device and cutting the portion of the breast tissue distal to said hooked guide wire to separate a portion of said breast tissue containing all of said lesion; and (j) removing the PEBB device containing said lesion.

In yet another variation of the method, the following steps are conducted after a localizing needle and hooked guide wire have been previously implanted to the desired locations:

(a) making a small incision on the surface of the breast at the point where a localizing needle enters the breast;

(b) passing a PEBB device over said localizing needle;

(c) inserting said PEBB device through said incision;

(d) further inserting said PEBB device and pushing aside the breast tissue;

(e) positioning said PEBB device to the desired location proximate said lesion;

(f) further inserting into the breast a first cutting surface of said PEBB device to the desired location near said lesion;

(g) manipulating a second cutting surface of said PEBB device and cutting the portion of the breast tissue distal to said hooked guide wire to separate a portion of said breast tissue containing all of said lesion; and (h) removing the PEBB device containing said lesion and the guide wire.

A further embodiment of the present invention features an apparatus for removing suspect breast tissue which comprises a stylet or obturator that has an open forward end (for receiving a guide wire), a rear end and an exterior surface. The apparatus also has a cannula which has an internal cavity defined by an interior surface, an open front end and a rear end. The cannula is dimensioned to receive the stylet within its internal cavity. The apparatus also includes driving means for driving the cannula forward of the open forward end of the stylet such that suspect breast tissue is receivable within the forward end portion of the cannula's internal cavity. Cutting means for cutting suspect breast tissue is positioned within the internal cavity.

In a preferred embodiment, the driving means includes a torsion assembly and a cam member. The torsion assembly is in driving engagement with the cannula and in contact with the cam member. The torsion assembly is preferably supported within a housing. Also, the torsion assembly includes a driving member and a torsion spring secured at one end to the driving member and at an opposite end to the housing. The aforementioned cam member includes a cylindrical casing with a cam channel formed therein while the driving member includes cylindrical extension with a drive channel formed therein. In addition, the torsion assembly further comprises a driving pin which is secured to the cannula, extends through the driving channel and is received within the cam channel.

In this particular embodiment, the driving means includes a spacing cylinder about which the torsion spring is wrapped. The spacing cylinder is in sliding contact with the driving member at a first end and in contact with the housing at a second end. The spacing cylinder including a through-hole through which the stylet extends, and the second end of the stylet is supported by the housing.

Activation means is provided to activate the driving means. The activation means includes a button slidingly supported by the housing and a pin member slidingly supported by the driving member when the pin is in a first position. The engagement pin is dimensioned and arranged such that a sliding of the button causes disengagement of the engagement pin with respect to the drive member and a release of potential energy in the torsion spring.

A cutting means for this embodiment includes a wire and the cannula includes a circumferential recess formed in the interior surface of said cannula at the forward end of the cannula. A longitudinal channel extends rearwardly from the forward end of the cannula and the channel and recess are dimensioned and arranged so as to receive the wire which is looped so as to conform with the circumferential recess in the forward end of the cannula. The wire has a first end fixed to the cannula at a position rearward of the loop and a second end in driving engagement with the driving means such that upon activation of the driving means, the loop of wire is contracted in cutting fashion.

The driving means includes means for rotating the cannula while the cannula is being driven forward of the stylet. The stylet is designed to include a convergently tapering front end section which slopes inwardly at an angle of 20° to 60° off the center line, and the open front end of the cannula includes a convergently tapering front end section which slopes inwardly at an angle which is essentially equal with the tapered front end of the stylet. The interior surface of the cannula is preferably cylindrical in shape with a maximum diameter of 7 to 15 mm. The tapered stylet or obturator thus provides penetrating means for penetrating the breast tissue while the sharp edged cannula provides first cutting means for cutting the breast tissue. The first cutting means is in sliding engagement with the penetrating means.

The looped wire provides a second cutting means for cutting breast tissue which is positioned at a forward end of the tissue receiving cavity for implementing a cut essentially transverse to the direction of sliding of the first cutting means. This latter embodiment of the present invention provides an advantageous method for removing suspect breast tissue which comprises inserting the penetrating member to a position behind a suspect breast tissue region and then activating the driving member so as to drive the first cutting means forward of a forward end of the penetrating member and forward of the suspect breast tissue region. The activating of the driving member further resulting in activation of a second cutting means when the first cutting means is driven forward of the suspect breast tissue region such that a removable cut-out core of breast tissue is provided.

A significant advantage of the present invention lies in the ability to achieve proper positioning of the cannula with respect to the lesion. In the present invention, the PEBB device is slid along the previously positioned guide wire and a clamping device maintains the PEBB device in proper position with respect to the guide wire which is made taught by the clamping device. The PEBB is placed in its activation position by aligning a suitable marker on the PEBB with a marker on the guide wire. As the amount of forward driving of the cannula and the length between the guide wire marking and the guide wire's internal tip is known, there is assured that the forward end of the cannula will be at the appropriate location past the lesion. Also, a mammogram can be conducted while the PEBB is properly positioned with respect to the guide wire marking so as to confirm that the hook of the guide wire is properly positioned. Once proper positioning of the hook is confirmed, the PEBB can be immediately fired. In this way the chance of having the hook move to a different location between the time of checking the location and actual removal of the lesion is avoided.

Further objects of the present invention will become apparent to those skilled in the art upon a study of the following specification, appended claims, and accompanying drawings.

BRIEF DESCRIPTION OF THE DRAWINGS

FIG. 9 shows a top planar view of another embodiment of the present invention;

FIG. 10 shows an elevational front view of that which is shown in FIG. 9;

FIG. 11 shows a cross-sectional view taken along cross-section line XI—XI in FIG. 12;

FIG. 12 shows a cross-sectional view taken along cross-section line XII—XII in FIG. 10;

FIG. 13 shows an enlarged view of the circle segment shows in FIG. 12;

FIG. 14 shows a partially broken away, perspective view of the stylet forming part of the present invention;

FIG. 15 shows a perspective view of the cannula forming part of the present invention;

FIG. 16 shows a partially cut away, perspective view of the components in FIGS. 14 and 15 in an assembled state;

FIG. 17 shows a partially cut away, perspective view of the assembly of FIG. 16 together with a driving member and additional components;

FIG. 18 shows a top planar view of the driving member in FIG. 17;

FIG. 19 shows an elevational rear view of that which is shown in FIG. 18;

FIG. 20 shows a cross-sectional view taken along cross-section line X—X in FIG. 18;

FIG. 21 shows a perspective view of the housing and end plugs which form a part of the present invention;

FIG. 22 shows a perspective view of the cam cylinder which forms a part of the present invention;

FIG. 23 shows the opposite side of that which is shown in FIG. 22;

FIG. 24 shows a side elevational view of the frame structure of an alternate embodiment of the cam cylinder;

FIG. 25 shows an elevational rear view of that which is shown in FIG. 24;

FIG. 26 shows a cam sheet for attachment with the frame structure of FIG. 24;

FIG. 26A shows an alternate embodiment of a cam track in which the driving pin follows;

FIG. 26B shows a cut-away, cross-section of the power spring in FIG. 26A;

FIG. 27 shows a top plan view of the alternate embodiment of the cam cylinder;

FIG. 28 shows a partially cut away view of the present invention with the alternate embodiment of the cam cylinder in place;

FIG. 28A shows a view similar to that of FIG. 13 except for the cannula having been driven forward;

FIG. 29A shows a cross-sectional and cut away view of one embodiment of the forward end of the stylet;

FIG. 29B shows an alternate embodiment of that which is shown in FIG. 29A;

FIG. 30A-30E shows sequential stages of use of the present invention;

DETAILED DESCRIPTION OF THE INVENTION

Figure 7:
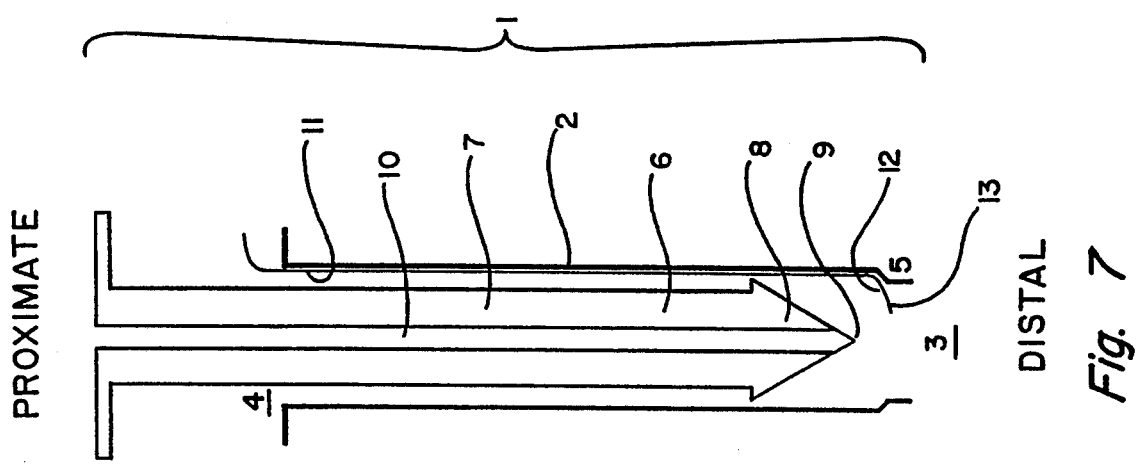
FIG. 7 is a view of the PEBB device.

With reference to FIG. 7, there is shown a PEBB device 1 which is preferably rigid. The PEBB device includes a cannula 2. Both the distal end 3 and proximate end 4 are open. The distal end 3 has a sharp cutting surface as at 5. The stylet 6 corresponds generally in shape to the cannula 2. The cylindrical shaft 7 of the stylet 6 has a tapered pointed distal puncturing end 8 which terminates in a point 9. The stylet or obturator 6 has a hollow central shaft 10 through which a localizing needle (not shown) can pass through and out the tapered pointed distal puncturing end 8. A descending element 11 fits between the cannula 2 and the stylet 6; all three elements fitting together tightly but allowing sufficient room for movement of the three elements. Descending element 11 optionally has a means at the proximate end for being rotated. The distal end 12 of the descending element 11 is a flexible steel cutting edge 13. It should be noted that the components of the PEBB device may be constructed of standard materials commonly used in the manufacture of surgical instruments. For example, stainless steel, polyurethane, suitable plastics of any other suitable surgical material may be employed. The PEBB device may be of any diameter, preferably 3 mm to 20 mm, and most preferably 10 mm. When plastics are used they can be transparent or opaque, slightly flexible or rigid.

Though the apparatus is shown as being cylindrical, other shapes are possible.

Localization techniques are necessary to identify nonpalpable abnormalities before biopsy. One technique involves use of a radiopaque hooked guide wire which has been placed through a localizing needle after the coordinates of the lesion have been determined by mammography. Virtually any imaging technique that provides multi-dimensional (e.g., sterotopic), localization of a lesion can be used to guide a localizing needle (for example, see U.S. Pat. No. 4,784,134). There are a variety of imaging techniques known in the art that can be used for needle guidance during biopsy. These techniques include fluoroscopy, ultrasound and computed tomography. Even magnetic resonance can be used with needles made from a special stainless steel. The choice of which modality to use is based on lesion size, position, and visibility; equipment availability; and the skills and preference of the individual radiologist or other trained personnel.

Figure 1:
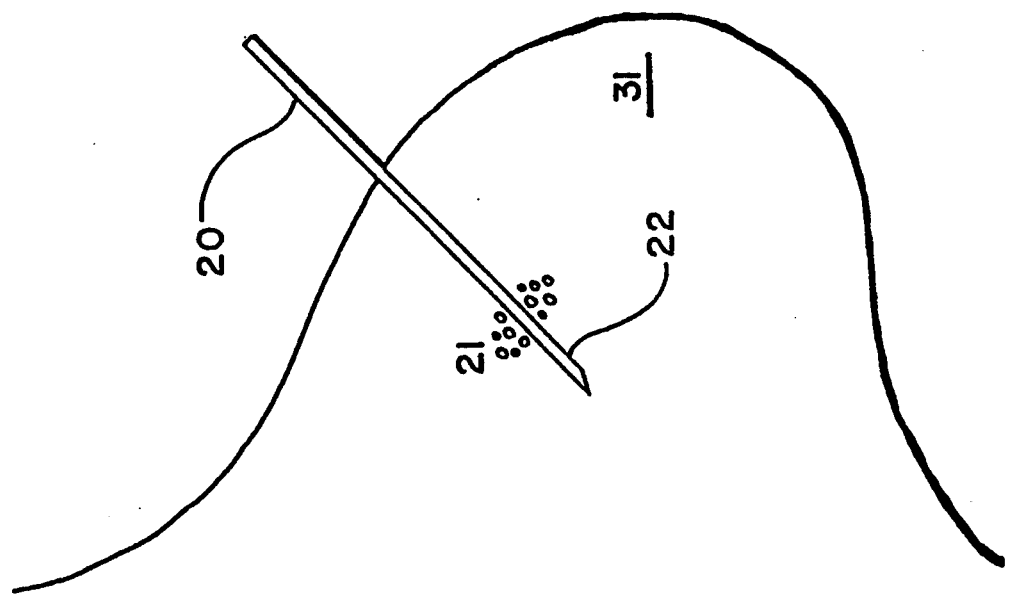
FIG. 1 is a simplified section of a human breast showing a localizing needle which has been passed distal to the breast lesion.

The hooked guide wire technique for localization of lesions is well known in the art (*Cancer of the Breast.*, W.L. Donegan and J. S. Spratt, 1988, pages 157–158). Using data from previous mammograms, the localizing needle 20 in FIG. 1 is inserted into the breast 31 at the approximate site of the lesion 21 (*Breast Diseases*, edited by J. R. Harris, S. Hellman, I. C. Henderson, and D. W. Kinne, 1987, pages 82–83). Through repeated mammograms and adjustment of the needle 20, the needle tip 22 is placed through and distal to the lesion 21, where the term "distal" means a location after the lesion (i.e., under or above, depending on patient position). Standard localizing needles of various sizes can be utilized, for example 18 to 28 gauge. The choice of needle type and size depends on the size, type, and location of the lesion and the preference of the radiologist.

Figure 2:
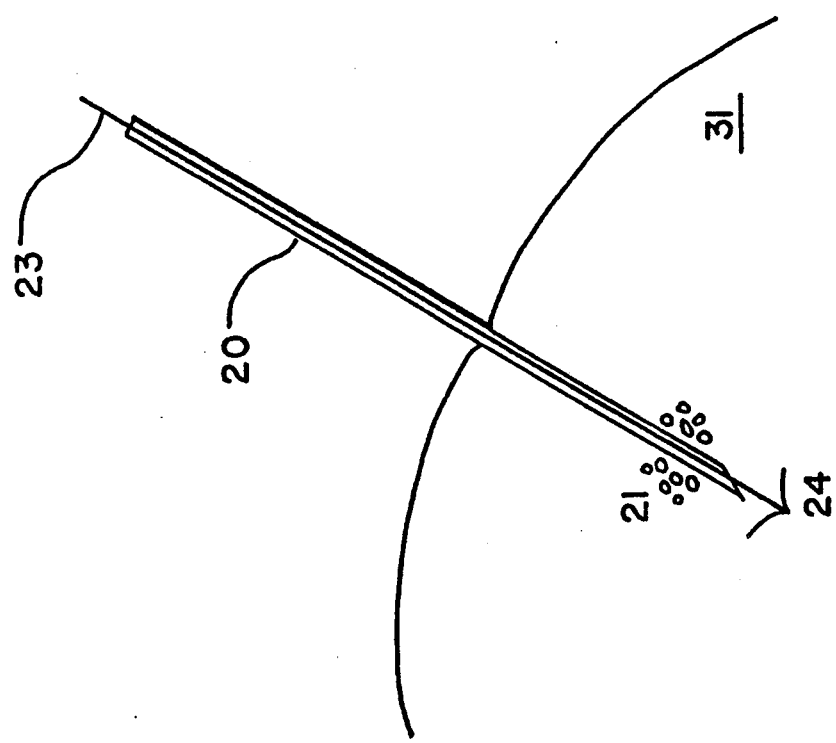
FIG. 2 is a view of the localizing needle through which a hooked guide wire has been passed.

In FIG. 2, a hooked or anchoring guide wire 23 is inserted through the localizing needle 20. Preferably, the hooked guide wire 23 has been preloaded into the localizing needle 20 prior to the localizing needle being implanted into the breast. The hooked guide wire 23 is further inserted through the localizing needle 20 whereupon the hooked end 24 of the hooked guide wire 23 immediately expands. The hooked end 24 of the hooked guide wire 23 is then lodged at the desired point where it anchors itself in the surrounding breast tissue. The hooked end 24 of the hooked guide wire 23 provides a relatively stable, anchored guide and serves as a means to locate the lesion 21 when the biopsy takes place. The biopsy may be immediately conducted or it may be conducted at another time or place.

The hooked guide wire 23 may be made of stranded spring steel or any other metal which has a memory (i.e., when the hooked guide wire is place in tissue, and is no longer constrained by the localizing needle, it resumes its original form); it is radiopaque. The hooked guide wire 23 is resilient in order that it may be compressed and loaded through the localizing needle 20. The hooked guide wire is preferably preloaded in the localizing needle prior to biopsy. The hooked guide wire may be of standard length (15–30 cm) and standard size diameter.

Figure 8:
FIG. 8 is a view of a specially designed hooked guide wire.

The hooked guide wire may be of standard design or it may be as hereinafter described. The specially designed hooked guide wire may have 2 to 8 arms (FIG. 8).

Figure 3:
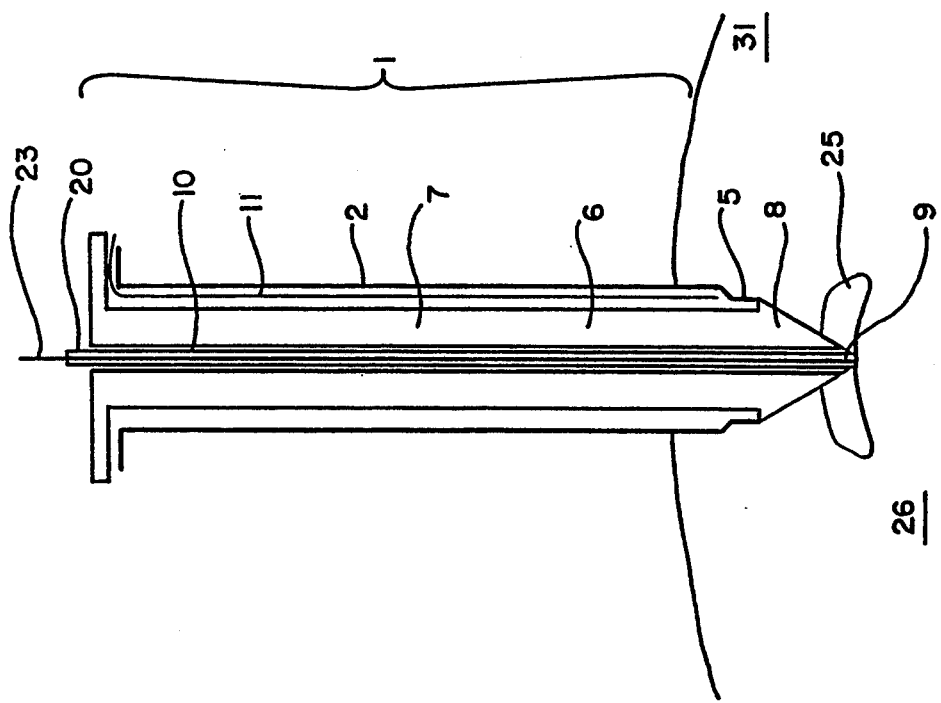
FIG. 3 is a view of the PEBB device which has been placed over the localizing needle and which is entering the breast through a small incision.

In FIG. 3, when the biopsy is to be performed, the surgeon makes a small incision 25 in the breast skin 26 along the implanted localizing needle 20 which contains the hooked guide wire 23. The size of the incision must be sufficient to allow entry of the PEBB device 1, generally the incision is approximately 7 mm to 20 mm. Local anaesthesia can be utilized. The PEBB device 1 is passed over the localizing needle 20 and hooked guide wire 23 by inserting the localizing needle 20 and hooked guide wire 23 through the tapered pointed distal puncturing end 8 and hollow central shaft 10 of the stylet 6. The tapered pointed distal puncturing end 8 of the stylet or obturator enters the breast 31 through the incision 25 that has been made.

Figure 4:
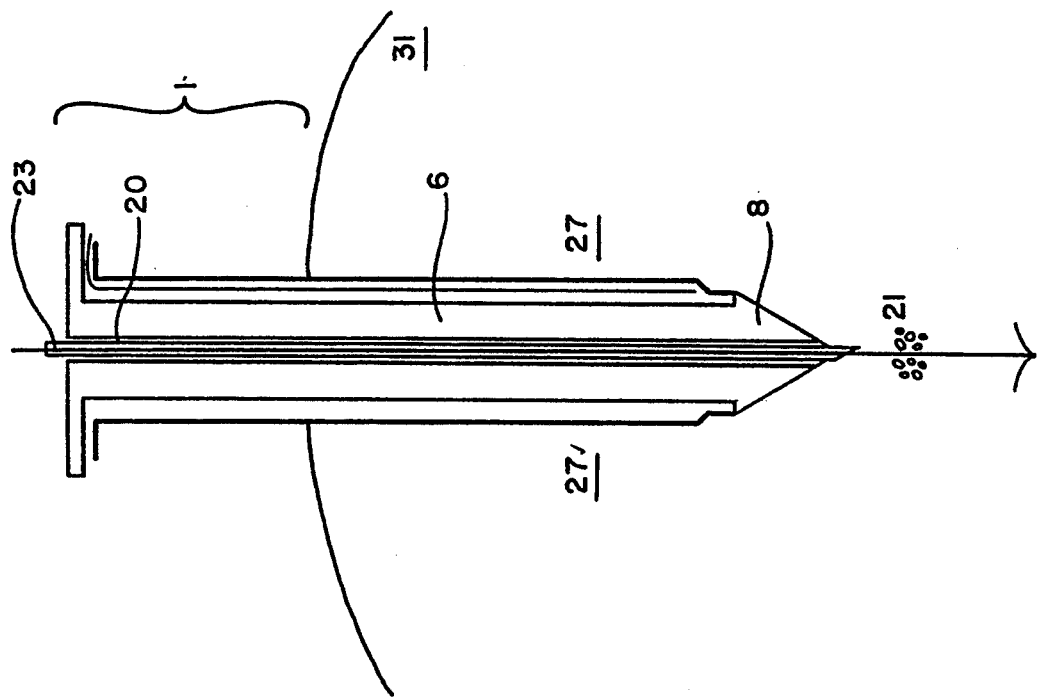
FIG. 4 is a view of the PEBB device passing into the breast along the localizing needle and stopping proximate the lesion and the hooked guide wire.

In FIG. 4, the tapered pointed distal puncturing end 8 of the stylet or obturator 6 bluntly separates the breast tissue 27. The PEBB device 1 is advanced towards the lesion 21 and is stopped proximate the lesion 21, where the term "proximate" means a location before the lesion (i.e., under or above, depending on patient position). The PEBB device may be rotated while it is being advanced. The PEBB device 1 is generally stopped 1 to 4 cm before the lesion.

Figure 5:
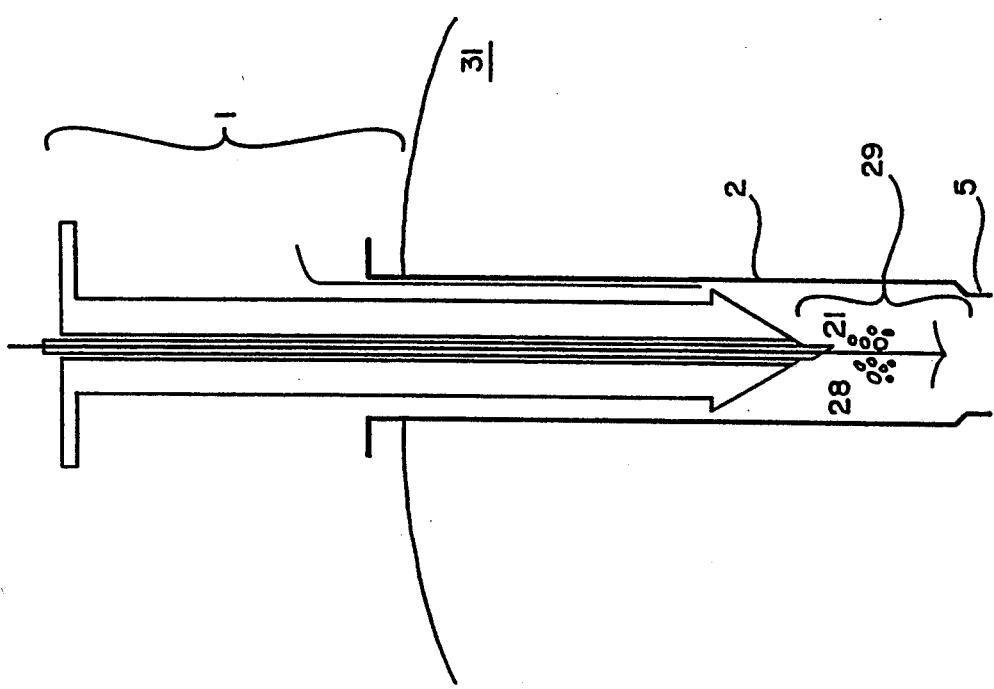
FIG. 5 is a view of the cannula of the PEBB device extended distal to the lesion and the hooked guide wire.

The position of the PEBB device 1 is confirmed by mammography. In FIG. 5, the cannula 2 of the PEBB device 1 is advanced distal the lesion 21, the sharp cutting device 5 thereby cutting the breast tissue 28 surrounding the lesion 1 as the cannula 2 is being advanced. The cannula 2 can be rotated in order to aid cutting. A mammogram is conducted to confirm that the lesion is in the chamber 29 formed by the cannula 2.

Figure 6:
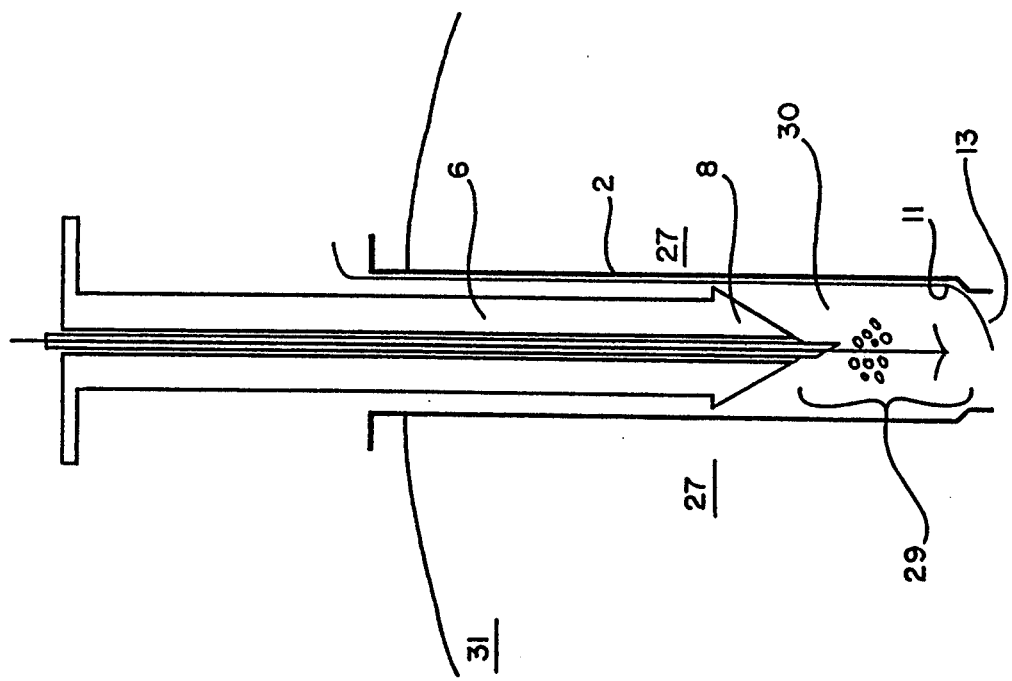
FIG. 6 is a view of the flexible steel cutting edge cutting the tissue distal the lesion and the hooked guide wire.

In FIG. 6, the descending element 11 is then pushed down in order for the flexible steel cutting edge 13 to internally cut the bottom of the biopsy specimen 30. The descending element 11 is rotated 360 degrees to completely cut the bottom of the biopsy specimen 30. The PEBB device 1 is then removed, taking along with it the biopsy specimen 20 in the chamber 29 formed by the cannula 2. Because the tapered pointed distal puncturing end 8 of stylet 6 bluntly separates the breast tissue 27 from incision 25 to lesion 21, this intervening breast tissue 27 is not removed.

FIG. 9 shows a top planar view of an alternate embodiment 48 of the present invention in position over guide wire 50. Guide wire 50 includes barb or hook end 52 which is positioned just past the lesion in the same manner previously described. PEBB device 48 includes cannula 54 which comprises small diameter section 53 having conical forward end 56 which forms a first cutting surface. FIG. 9 also illustrates stylet or obturator 58 having a tapered puncturing end 60 with opening 62 formed therein. Opening 62 receives guide wire 50 as shown in FIG. 12. Cannula 54 extends into and is received by housing 64 which has front plug 66, outer casing 70 and back plug 80. Fasteners 68, 68' and 82, 82' are used to connect front and back plugs 66 and 80 to outer casing 70 of housing 64. FIG. 9 also illustrates release button 76 having engagement pin 78 extending therethrough as well as recess 74 formed in casing 70 of housing 64. FIG. 9 further illustrates guide wire 50 extending out the back end of housing 64 as well as garret wire 88 extending out of the back housing and having stop bead 90 at its rearwardmost end.

FIG. 10 shows a front elevational view of that which shown in FIG. 9 except with guide wire 50 removed. As shown in FIG. 10, fasteners 68, 68' are diametrically opposed while tapered puncturing end 60, tapered front end 56 and the remainder of cannula 54 are concentrically arranged.

FIG. 12 show a cross-sectional view taken along cross-section line XII—XII in FIG. 10. FIG. 12 illustrates guide wire 50 and barb 52 following passage through lesion 21. The forward open end 62 of tapered puncturing end 60 is positioned just rearward of lesion 21. As described for the previous embodiment, the forwardmost end of guide wire 60 is placed just forward of lesion 21. Guide wire 50 passes through open end 62 of cylindrical shaft 59 which forms a part of stylet 58. Shaft 59 is an elongated member preferably having an outside diameter of 7 mm and a longitudinal length of about 7.5 inches (19.05 cm). The tapered puncturing end 60 provides 3 to 10 mm of the overall longitudinal length of stylet 58. The distance between the tip of guide wire 50 and guide wire marking 51 is preferably about 9 to 10 inches (22.86 to 25.40 cm).

Small diameter section 53 of cannula 54 is in the form of an elongated cylinder having an interior surface in sliding engagement with the exterior of cylindrical shaft 59. The forwardmost end of smaller diameter section 53 includes a forward edge cutting surface 56 which tapers to a sharp edge. Preferably, the forward edge 56 of section 59 tapers at an angle similar to the taper of puncturing end 60. Cannula 54 also includes larger diameter section 55 which is integral with smaller diameter section 53 so as to form step shoulder 61. Cannula 54 is received within housing 64 such that step shoulder 61 is commensurate with the forwardmost surface of front plug 66.

Fastener 68 and 68' are illustrated in FIG. 12 as extending through outer casing 70 and cam cylinder 86 so as to fix them in position with respect to front plug 66. FIG. 12 also illustrates engagement pin 78 extending through release button 76, through block support 98 and into base 93 of driving member 91. Driving member 91 features cylindrical extension portion 95 which includes longitudinally extending drive channel 92. Drive channel 92 extends from the forwardmost end of cylindrical extension 91 to a position just forward or commensurate with the forward end of base 93.

FIG. 12 also illustrates driving pin 94 fixedly secured to larger diameter section 55 of cannula 54. Driving pin 94 extends through drive channel 92 and into cam channel 158 which is described in greater detail below. Driving pin 94 preferably features hole 96 through which garret wire 88 is threaded.

As illustrated in FIG. 11, base member 93 of driving member 91 includes hole 124 through which garret wire 88 is further threaded.

With reference again to FIG. 12, securement means 101, which is preferably in the form of a pin, passes through cylindrical shaft 59 and into spacing cylinder 102. Pin member 101 can be adhered to and/or frictionally wedged in place with respect to corresponding diametrically opposed holes formed in spacing cylinder 102. Spacing cylinder 102 has a forward end in contact with the rearward end of base member 93 and a rearward end in contact with the forward end of back plate 80.

In order to allow for rotation of cannula 54, at least one end of spacing cylinder 102 is frictionally contacting and not rigidly secured to the adjacent contacting surface. In a preferred embodiment both ends of spacing cylinder 102 are merely in frictional contact with the adjacent surfaces of base 93 and back plug 80. Low friction coefficient material such as TEFLON ™ or the like can be provided at the contacting surfaces so as to facilitate rotation of driving member 91.

Back plug 80 further includes threaded recesses that are sized to receive fasteners 82, 82' which secure the rear end of outer casing 70 to back plug 80. In one embodiment of the invention, back plug 80 includes a hole through which the rear end of garret 88 is threaded. This hole is sufficiently large enough so as to enable garret wire 88 to slide therein but sufficiently small enough to prevent bead 90 from passing therethrough.

Torsion spring 130 is shown encircling spacing cylinder 102 and has its forward end secured to the rearward end of base member 93 and its rearward end secured to the forward end of back plug 80. FIG. 12 also illustrates guide wire marker 51 formed on guide wire 50 and shown in FIG. 12 to be commensurate with the rearward end of back plug 80. Guide wire marker 51 can take any form but preferably is a painted circle or a spot provided a predetermined distance from the forwardmost end of guide wire 50 for reasons to be explained in greater detail below.

FIG. 11 illustrates a cross-sectional view taken along cross-section line XI—XI in FIG. 12. As shown in FIGS. 11 and 12, release button 76 bridges aperture 72 and has a forward end in sliding contact with a forward section of recess 74 and a rearward end in sliding contact with a rearward section of recess 74. Sliding block 98 is designed to slide along notch planar surface 100 formed in base member 93. Notch planar surface 100 of base member 93 also includes an engagement pin notch 122 which extends rearwardly and opens out to the back end of base member 93. (See FIGS. 17-19).

Figure 33:
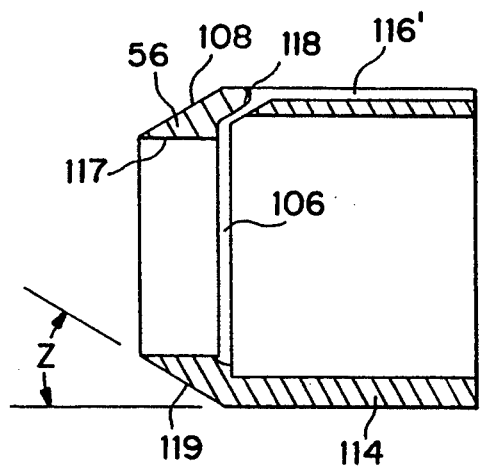
FIG. 33 shows an enlarged cross-sectional view of the cannula forward end.

FIG. 13 illustrates an enlarged view of the circled region of FIG. 12 at the forward end of cannula 54. As shown in FIG. 13, the forwardmost end of guide wire 50 is positioned forward of the forwardmost end of breast abnormality or lesion 21. Barb 52 acts to fix guide wire 50 in position with respect to abnormality 21. Guide wire 50 extends through opening 62 formed at the forwardmost end of tapered protruding end 60 of stylet 58. Cannula 54 features outer shell 120 and inner cylindrical member 110 securely fixed to shell 120. Inner cylindrical member 110 includes step shoulder 112 at its forward end and forwardly extending flange 113. Inner cylindrical member further includes longitudinal channel 116 within which extends garret wire 88. Cap 108 is securely fixed between outer cover 120 and inner cylindrical member 110. Cap 108 includes cap extension 114 which contacts step shoulder 112 so as to form cylindrical recess 106 between the forwardmost end of inner cylindrical member 110 and an internal surface of cap 108. Cap member 108, outer shell 120 and inner member 110 are preferably adhered or otherwise secured together to form a single unit. Cap member 108 is further illustrated in FIG. 33. As shown in FIG. 33, channel member 116' is formed therein so as to coincide with channel 116 formed in inner cylindrical member 110. Cap member 108 includes cut away section 118 which extends from channel 116' to circular recess 106. Recess 106 provides a location for positioning of garret loop 104 shown in FIG. 13 and in greater detail in FIG. 28A. Cap 108 includes forward edge cutting surface 56 which is defined by tapered surface 119 and internal wall 117 shown in FIG. 33. FIG. 33 also shows tapered surface 119 forming angle Z with respect to the horizontal. Preferably, angle Z is about 20 to 60 degrees and more preferably 20 degrees.

FIG. 14 shows the stylet 58 alone with its tapering end 60 and opening 62. As shown in FIG. 14, tapering end 60 is formed as a continuous portion of cylindrical shaft 59 and preferably tapers either in a continuous manner or in a curved manner so as to form a horn shape. FIGS. 29A and 29B illustrate alternate embodiments of the present invention wherein plugs 172 and 172' are provided at the forward end of the cylindrical shaft 59. As shown in FIG. 29A, plug 172 includes a recess shoulder which receives the forward end of shaft 59 and is preferably adhered or otherwise fixed thereto. Plug 172 includes a forward penetrating surface 174 which preferably forms angle X with respect to the horizontal. Angle X preferably has the same dimensions as those of the unitary embodiment noted above (i.e., 20 to 60 degrees). In FIG. 29A, angle X is about 20 degrees. Plug 172 also include interior throughhole 178 which helps in the guiding of PEBB 41 along guide wire 50 (or along a localization needle if the needle is to be maintained in place during operation of the PEBB). FIG. 29B illustrates a similar arrangement as that of FIG. 29A except for forward penetrating surface 174' being less inclined than its counterpart in FIG. 29A. As shown in FIG. 29B, angle Y is about 60 degrees with respect to the horizontal.

FIG. 15 illustrates cannula 54 having smaller diameter section 53 and larger diameter section 55. Step shoulder 61 illustrates the differences in diameter between smaller diameter section 53 and larger diameter section 55, which can either be formed as separate members or more preferably as a single unitary body. FIG. 15 further illustrates forward cutting surface 56 forming part of cap 108. Interior surface 117 as well as the interior surface of inner member 110 (FIG. 13) is designed to slidingly receive the exterior of cylindrical shaft 59 of stylet 58. Driving pin 94 is shown extending off from larger diameter section 55 and threading hole 96 formed in driving pin 94 is also illustrated in FIG. 15. As explained in greater detail below, the driving pin works in conjunction with cam 86 and driving member 91 to provide driving means for driving cannula 54 forward with respect to stylet 58 which is maintained axially stationary by pin 101 (FIG. 12).

FIG. 16 shows the positioning of cannula 54 with respect to stylet 58. The frictional contact between cannula 54 and stylet 58 is sufficient to provide some degree of positioning ability such that the two members do not slide too easily during assembly. Cannula 54 is shown in FIG. 16 in its proper position, wherein the forwardmost end of cap 108 is aligned with the origin of tapering end 60 of stylet 58.

FIGS. 18–20 illustrate driving member 91 of the present invention. FIG. 18 shows a top planar view of driving member 91 which includes base 93 having upper notch section 100 and engagement pin notch 122. Extending forwardly off the forward end of base member 93 is cylindrical extension portion 95. Cylindrical extension portion 95 includes driving channel 92 which extends longitudinally from the forward end of base member 93 to the forwardmost end of extension member 95. Driving channel 92 is sized so as to slidingly receive driving pin 94. Driving member 91 includes a central aperture 126 which is sized so as to frictionally receive cylindrical shaft 59 and thus the aperture has a diameter essentially equal to the inside diameter of inner member 110 and the inside diameter of cylindrical shaft 102. As shown in FIG. 12, back plug 80 also includes a central aperture which is similarly sized so as to snugly receive shaft 59. Interior wall 128 of driving member 91 defines a larger diameter than the diameter defined by aperture 126 and receives the exterior surface of the cannula's larger diametered section 55 in sliding fashion.

FIG. 17 illustrates the positioning of driving member 91 onto the exterior surface of larger diametered section 55 as well as the positioning of driving pin 94 within driving channel 92. FIG. 17 also provides a partially cut away view of stylet 58 surrounded by spacing cylinder 102 which, in turn, is surrounded by torsion spring 130. Torsion spring 130 is shown in FIG. 17 to be in the form of a helical type spring. Various other torsion springs can also be relied upon or alternately, a power spring can be used as explained in greater detail below.

FIG. 21 illustrates the preassembled state of housing 64 together with cam cylinder 86 in position. As shown in FIG. 21, front plug 66 includes exterior flange 132 and interior member 134 having threaded hole 136 formed therein. Interior member 134 is designed to fit within the interior surface of cam cylinder 86 which is frictionally received by the interior surface of outer casing 70. Outer casing 70 includes threaded hole 138 and cam cylinder 86 includes threaded hole 139 (see FIG. 22) which can be aligned together with threaded hole 136 so as to receive fastener 68 (FIG. 12). Corresponding threaded holes are formed diametrically opposed to thread holes 136, 138 and 139 so as to receive fastener 68'. The rear end of outer casing 70 includes threaded hole 140 and a corresponding threaded hole 148 is formed in back plug 80. Back plug 80 includes exterior flange 142 and interior member 144. Interior member 144 includes a central aperture 146 which receives the rear end of stylet 58. Interior member 144 can also optionally include garret wire hole 150. Torsion spring securement means 152 is shown in FIG. 21 fixed to interior member 144. The exterior diameter of interior member 144 is dimensioned so as to frictionally contact the interior surface of outer casing 70. The securement of fasteners 82 and 82' results in back plug 80 being fixedly secured to the rear end of outer casing 80. The forwardmost surface 155 of inner member 144 is positioned such that the rearward end of spacing cylinder 102 is frictionally engaged therewith. Similarly, the forward end of spacing cylinder 102 is frictionally engaged with the rearward end of base member 93. Back plug 80 could also be threadably engaged with casing 70.

FIGS. 22 and 23 provide two different views of one embodiment of cam cylinder 86. Cam cylinder 86 includes front end 154 and rear end 156 as well as cam channel 158. Cam channel 158 includes a forward curve portion 160 which leads to partial circumferential section 162 of cam channel 158. The curved portion provides for a 120° or more rotation of the cutting cannula. Section 162 of cam channel 158 ends at 164 to provide a stop for driving pin 94.

FIGS. 24–27 illustrate an alternate embodiment (86') of the cam cylinder. As shown in FIGS. 24 and 25, cam cylinder 86' features a partially cylindrical frame structure 166. FIG. 26 illustrates flexible material sheet 168 which is dimensioned such that when wrapped within the interior of frame structure 166 it forms cam channel 170 in the manner shown in FIG. 27. The driving pin can be dimensioned so as to slide within cam channel 170 and upon reaching the end of cam channel 170 slide along the interior surface of frame structure 166.

FIG. 28 illustrates a partially cut away, top planar view of an alternate embodiment of the present invention which includes modified cam cylinder 86'. As shown in FIG. 28, garret wire 88 includes a first end 188 which is secured to the exterior of interior member 110 (or is received within an aperture formed therein). Adhesive area 184 represents one manner of securing first end 188. Garret wire 88 extends from its secured end 188 to hole 186 defined by slot 118 (see FIG. 28A). The garret wire is then looped within recess 106 and extended back through hole 186 and along channel 116 through larger diameter section 55 via hole 103 (FIG. 15). Garret wire 88 extends out of larger diameter section 55 into driving channel 92 and through hole 96 as formed in pin 94 as shown in FIGS. 12 and 28. Garret wire 88 then passes through base member 93 and into the open chamber formed at the rear end of casing 70 as shown in FIG. 28 or, alternatively, extends completely through the rear chamber formed in the rear end of casing 70 and through back plug 80 as shown in FIG. 12. As shown in FIG. 28 temporary securement patch 90' formed of wax or the like can be applied to housing 70 to hold wire 88 in position until PEBB 48 is activated.

FIG. 26A shows an alternate embodiment of the cam cylinder which is designated 86'' in the figure. As in the prior embodiments, cam cylinder 86'' includes a cam channel (an acme thread groove in this case) in which driving pin 94' travels. This arrangement allows for an increase in the number of turns and garret wire take up for a given axial length of the cam cylinder 84''. With this arrangement four complete turns of the cannula are possible for achieving the cutting action. The pin and cam cylinder are arranged so that after the end of four turns within the cam channel the driving pin rotates freely for at least one more turn against the edge of the cam cylinder so as to take up the garret loop. Driving member 91' includes a spring attachment section 306 which is dimensioned such that power spring 130' coils around it. FIG. 26B shows the coiled nature of power spring 130' secured to attachment section 306 at one end and fixed housing 70 at the other end. Section 306 also takes the place of the previously described spacer. Power spring 130' has one end secured to the fixed interior of the housing with fasteners 300 and its other end fixed to rotatable driving member 91' with fasteners 306. Power spring 130' can be coiled prior to fastening the back plug and maintained in place with the engagement pin. The engagement pin is then released such that spring 130' uncoils to provide at least 5 lbf is provided at or near the end of travel for drive pin 94' to ensure that the garret loop achieves its cutting function.

FIG. 28A illustrates the final position of cutting surface 108 following activation of the PEBB device at a point just prior to garret loop 104 being made taught in the manner described in greater detail below. As can be seen, garret loop 104 is positioned sufficiently forward of tip 52 of wire 50 to avoid entanglement during contraction of the loop. To ensure that the anchored guide wire will be removed together with the core sample, the material forming the entire cannula 54 (or at least the end region of the cannula) is formed of a radiographic transparent material. In this way, a radiographic check can be made to ensure that the forward end of the cutting cannula is sufficiently forward of the guide wire anchors such that the entire guide wire will be removed when the core sample is removed.

Operation

FIGS. 30A to 30E illustrate the present invention's sequential steps when using PEBB device 48. The free end of guide wire 50 is threaded through PEBB device 48 in the manner illustrated in FIG. 30A. FIG. 30A illustrates guide wire 50 after having been placed in proper position and verified as being in the proper location in the manner previously described. FIG. 30A further illustrates breast 190 in a compressed state between film plane 192 and compression panel 194 in the manner well known in the art. PEBB device 48 is guided along guide wire 50 until the rear end of PEBB device 48 is commensurate with marking 51 formed on guide wire 50 in the manner illustrated in FIG. 30B. As shown in FIG. 30B, during the positioning of PEBB 48, tapered stylet 58 and cannula 54 penetrate the breast (preferably following a small incision being made to lessen skin surface tension). The degree of penetration will vary depending upon the location of the lesion within the breast. In any event, once marker 51 is matched with the corresponding reference point on PEBB 48, the distance from tip 52 of wire 50 to the forward end of styler 58 is a known value. PEBB 48 can be clamped into position with respect to guide wire 50 by use of clamp 84' (FIG. 9) which can take any form such as those presently used to maintain the guide wire in position with respect to the exterior of the breast. Once it is determined through a mammogram check that PEBB 48 is in proper position, release button 76 is activated by moving release button 76.

With reference now to the previously discussed figures, such as FIG. 12, the backward movement of release button 76 results in engagement pin 78 sliding out of notch recess 122. Torsion spring 130 is preset to a degree of torsion based on the amount of twisting involved in lining up back plug 80 (which is attached to the rear end of torsion spring 130) and fasteners 82 and 82'. Once released from its pre-torsion state, the potential energy in torsion spring 130 is released in a manner which causes driving member 91 to rotate. The rotation of driving member 91 causes driving pin 94 and attached cannula 54 to move forward and in a spiral fashion with respect to stylet 58 while driving pin 94 (or 94') follows or moves within cam channel 158 (or within the grooves provided in cam cylinder 86' or 86'') and driving channel 92.

In the embodiment shown in FIG. 12, once driving pin 94 reaches the end of driving channel 92, the driving pin is free to rotate within the circumferential portion 162 of cam channel 158. In cam cylinder 86', sheet 168 is made shorter than frame 166 such that pin 94 is free to rotate with the unwinding torsion spring along the interior surface of the forward end 167 of frame structure 166. In cam cylinder 86'', the spiral track allows for an adequate take up of garret wire 88 when driving pin 94 reaches the end of the spiral track.

The forward driving motion and the spiral motion imposed on driving pin 94 results in cannula 54 being both driven forward and rotated. Cannula 54 thus drives through the breast so as to pass by lesion 21 as well as the barbed end of guide wire 52. The final positioning is illustrated in FIG. 28A. As the length from the tip of the hook to the guide wire marking is known and the length of the extension of the cannula from its pre-activation state to its postactivation state is known, precise positioning of the forward edge of the cannula is possible. The precise positioning only requires that garret loop 104 be placed forward of the forward tip of guide wire 50. A mammogram check prior to activation and while the PEBB is in position on the guide wire is possible so as to avoid the prior art difficulty of having the hook float or move to a different position within the period between the mammogram check and the placement of the patient at the surgical location. Clamps such as claim 84 in FIG. 9 which were used in the prior art in an attempt to lock the guide wire in position during movement of the patient during surgery, can also be used in the present invention either on the breast surface or as part of the PEBB to maintain the guide wire taught and at the guide wire mark location.

While cannula 54 is being driven forward and rotated, the rotation of driving pin 94 also causes garret wire 88 to be drawn inwardly until bead 90 abuts either the back member of plate 80 (FIG. 12) or the back member of base member 93 (FIG. 28) or some other stop. A continuation of the rotation of driving pin 94 within the circumferential portion of the cam channel while bead member 90 has reached its state of abutment, results in loop 104 being drawn inwardly up into slot 118 so as to achieve a full cut in a direction transverse to the axial center line of cannula 54. The length of the garret wire is such that the closing of the loop begins just as the cannula has reached its forward most extension which coincides with the guide wire's stop bead coming in contact with the stop member.

The closing of loop 104 (FIG. 28) results in a core sample of breast material being formed which has a longitudinal length extending from the cutting location of garret loop 104 to the forward surface of penetrating end 60 and a circumference defined by the interior surface of cylindrical member 110 extending between loop 104 and end surface 60. In a preferred embodiment, the interior diameter of interior member 110 is about 5 to 15 mm and more preferably 7 mm. Also, the longitudinal distance between the forwardmost tip 62 of stylet 58 and the cutting location of garret loop 104 (following activation of PEBB 48) is preferably 3 or more mm and more preferably about 3 mm. (Garret 50 is preferably formed of stainless steel and has a diameter of 0.005 inch to 0.008 inch.)

By decreasing the angle of incline of surface 60 it is possible to lessen the maximum longitudinal distance between cutting location of garret loop 104 and the rearward most portion of surface 60. The taper of surface 60 cannot be made too low, however, as there would be a resultant loss in the ease of penetration of penetrating end 60. A range of 20° to 60° with respect to the vertical is preferred.

Assurance that garret loop 104 cuts through the tissue at the time cannula 54 reaches its forwardmost position is provided by marking 51 on guide wire 50 which positions the cannula 54 prior to release of lever 76 in just the right location with respect to the lesion. Also, garret wire 88 is of a length which is sufficient to enable driving pin 94 to reach the end of the curved portion of cam channel at a time when stop bead 90 is placed in an abutting position while the continued release of torsion spring causes loop 104 to be taken up so as to cut through the breast material forward of the lesion.

FIG. 30C illustrates cannula 54 in the position shown in greater detail in FIG. 28A. PEBB device 48 of the present invention can be either hand held by gripping casing 70 or, alternatively, casing 70 can be positioned in a supporting holder (not shown). A suitable holder could be one that is fashioned somewhat like the holder and patient positioning system used with biopsy needle operations (e.g., the MAMMOTEST TM system of Medical Imaging Systems of Hanover, Md.). The support means of the stand would be modified to support the PEBB rather than the biopsy needle assembly.

FIG. 30D illustrates the drawing out of cannula 54 from breast 190. As illustrated in FIG. 30D, the drawing out of cannula 54 results in core 198 being removed from breast 190 but, since stylet 58 was the forwardmost member during initial positioning of PEBB 48, no further breast material is removed and the original passageway closes up forward of cannula 54 as it is being withdrawn from breast 190.

The core specimen 202 removed from breast 190 can then be ejected from PEBB 48 by rotation of cannula 54 and the forcing of cannula 54 rearward until stylet 58 achieves its original position. The entire PEBB device can then be withdrawn along guide wire 50 leaving core sample 202 in a preserving solution 204 such as contained in sample container 206 as shown in FIG. 30E.

Figure 31:
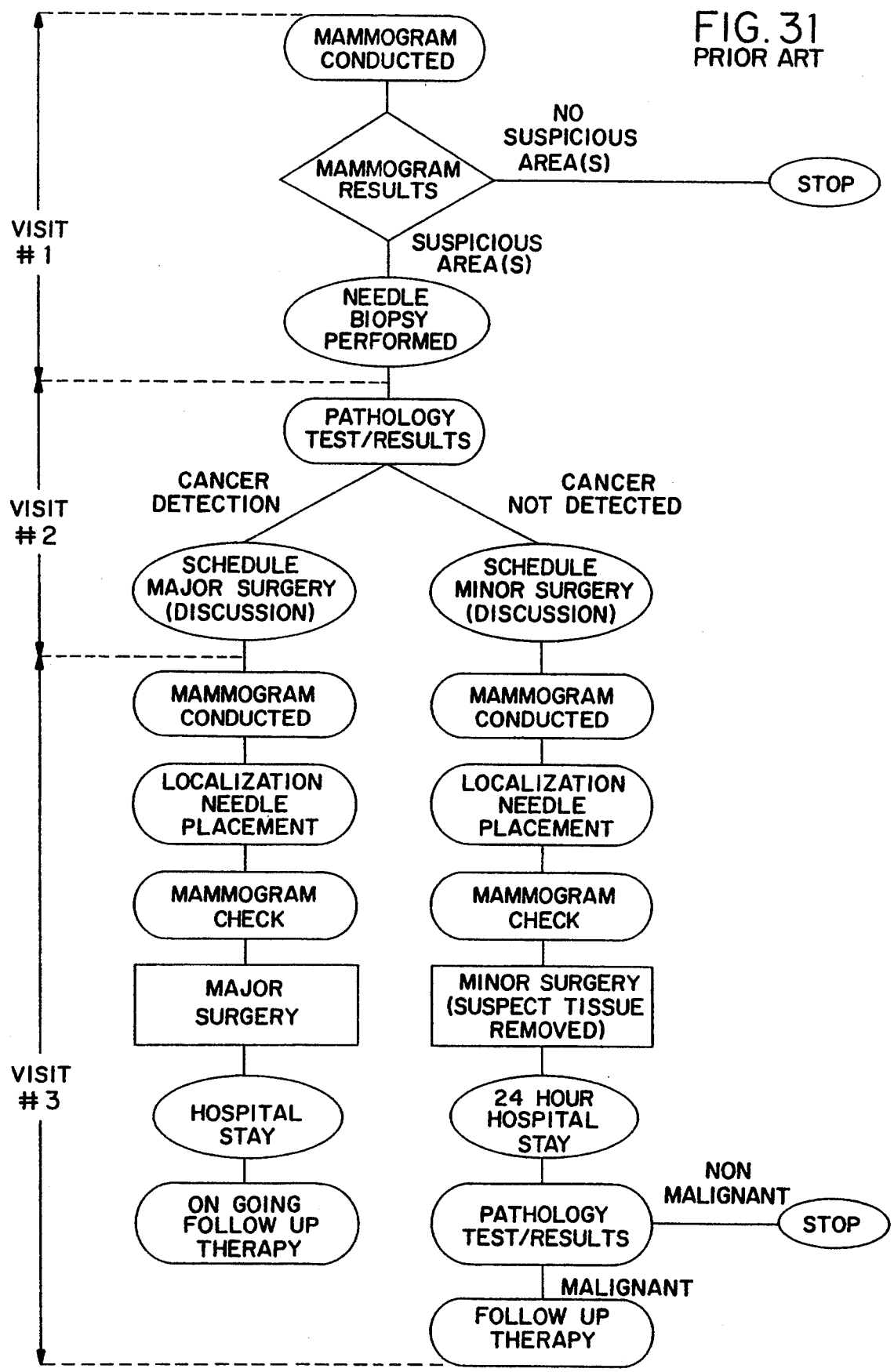
FIG. 31 shows a flow chart of the steps involved in a prior art technique.

FIG. 31 provides a flow-chart illustration of the sequential steps involved in a breast biopsy procedure utilizing the technique of the prior art. As shown in FIG. 31, a patient in her first visit has a mammogram conducted and a review of the mammogram results are made. If the review of the mammogram shows that no abnormalities exist, that is the end of the procedure. If, however, an abnormality is spotted, a needle biopsy is conducted either during this first visit or at a subsequently scheduled visit.

In the second visit the patient is informed of the pathology results. If the pathologist determines a malignancy exists, then major surgery (lumpectomy, mastectomy) is scheduled. If the pathologist determines that no malignancy exists in the sample, then minor surgery is scheduled (again, a needle biopsy test could provide a false negative reading as explained above).

If malignancy is detected, the patient is subject to a mastectomy procedure or a lumpectomy proceeding in a third visit.

In the lumpectomy proceeding (for smaller contained tumors) a mammogram is conducted followed by a localization procedure (localization needle and guide wire placement), a mammogram check and the removal of the localization needle. The tumor and guide wire are later removed in a surgical procedure. The patient is then released following recovery and scheduled for follow-up therapy.

In the mastectomy procedure, the patient is subjected to the same procedure as for the lumpectomy except that the major surgery is much more extensive so as to typically require an extended hospital stay.

Extensive follow-up therapy is then routinely conducted to monitor the situation.

If malignancy is not detected by the pathologist, a third visit is still scheduled for surgical removal of the tissue in question. A subsequent pathology is conducted to determine whether follow-up procedure is required.

Figure 32:
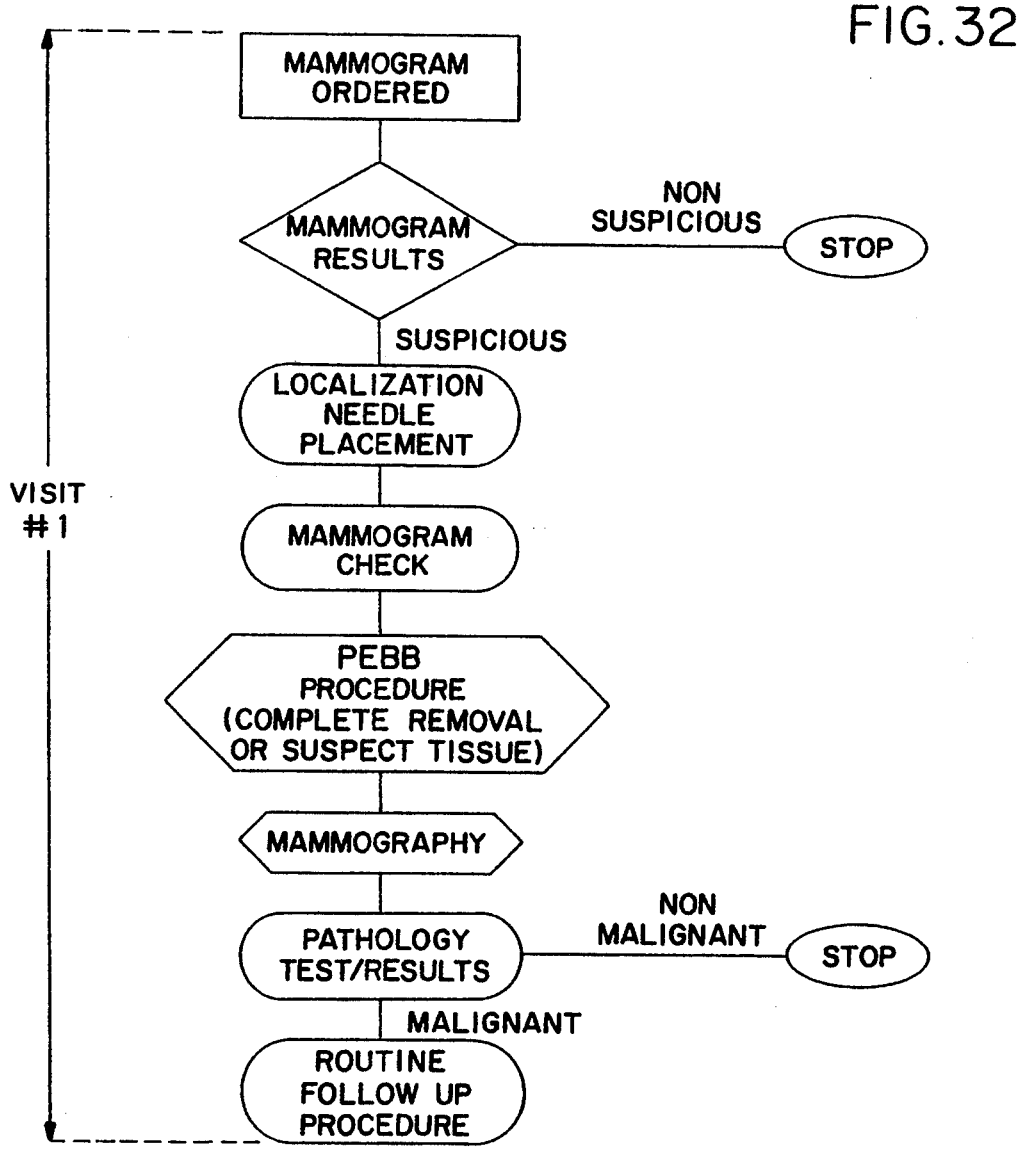
FIG. 32 shows a flow chart of steps included in the present invention.

FIG. 32 illustrates the procedure utilizing the present invention when the abnormality region is contained within a tissue area which is essentially 5 mm in diameter.

In accordance with the procedure set forth in FIG. 32, a mammogram is conducted and the results analyzed by a radiologist or a trained nurse. If the results show no abnormalities, the procedure is stopped. However, if an abnormality is found, a localization needle is placed in position followed immediately by a mammogram check to confirm proper positioning of the localization needle. Upon determination by way of a mammogram check that the localization needle is properly positioned, the localization needle is removed while retaining the guide wire in position and the above described PEBB procedure is conducted. Prior to removing the core sample a mammogram check can be made to ensure that the contracted garret loop is forward of the guide wire barbs, otherwise it would be difficult to remove the anchored guide wire. The cannula can be transparent to the mammography device to facilitate guide wire viewing ability. The sample taken is then studied or forward to a pathologist. If the sample taken contains all the abnormalities (which would be true for abnormality regions having the size described above), whether the results are positive or negative would not be of great concern as the potential problem area has been completely removed such that surgery is no longer required. In any event, a malignancy determination by the pathologist would involve the scheduling of a follow-up procedure to monitor the situation. If nonmalignant tissue is found, then the procedure is completed. Thus, for relatively smaller, contained lesions the present invention provides a procedure which can be completed by a single visit (followed by a subsequent telephone call or letter if the pathology test is not conducted at the same time as the visit) as opposed to the three or four visits required in the prior art procedure.

If the abnormal region has dimension larger than that described above, then the PEBB procedure provides a simplified manner of extracting a good sample for analysis followed by surgery if the test results show a problem.

It will be appreciated that the instant specification and claims are set forth by way of illustration and not limitation and that various modifications and changes may be made without departing from the spirit and scope of the present invention.

We claim:

1. An apparatus for removing suspect breast tissue, comprising:
    a stylet having a tapered forward end, a rear end and an exterior surface;
    a cannula having an internal cavity defined by an interior surface, an open front end and a rear end, and said stylet extending within said internal cavity;
    a driving assembly for rotating and driving said cannula forward of the forward end of said stylet such that suspect breast tissue is receivable within said internal cavity;
    a cutting device for cutting suspect breast tissue positioned within said internal cavity, said cutting device being in contact with said cannula and adapted to form a cut in the suspect breast tissue forward of the forward end of the styler.

2. An apparatus as recited in claim 1 wherein said driving assembly includes a torsion assembly and a cam member, said torsion assembly being in driving engagement with said cannula and in contact with said cam member.

3. An apparatus as recited in claim 2 further comprising a housing for supporting said driving assembly.

4. An apparatus as recited in claim 2 wherein said torsion assembly includes a driving member and a torsion spring secured at one end to said driving member and at an opposite end to said housing.

5. An apparatus as recited in claim 4 wherein said cam member includes a cylindrical casing with a cam channel formed therein, said driving member includes a cylindrical extension with a drive channel formed therein, and said apparatus further comprising a driving pin which is secured to said cannula, extends through said driving channel and is received within said cam channel.

6. An apparatus as recited in claim 5 wherein said driving means includes a spacing cylinder about which said torsion spring is wrapped, said spacing cylinder being in sliding contact with said driving member at a first end and in contact with said housing at a second end, said spacing cylinder including a through-hole through which said stylet extends, and the second end of said stylet being supported by said housing.

7. An apparatus as recited in claim 1 wherein said cutting device includes a wire and said cannula includes a circumferential recess formed in the interior surface of said cannula at the forward end of said cannula and a longitudinal channel extending rearwardly from the forward end of said cannula, said channel and recess being dimensioned and arranged so as to receive said wire whereby a loop of wire is formed at the forward end of said cannula, said wire having a first end fixed to said cannula at a position rearward of said loop and a second end in driving engagement with said driving assembly such that following activation of said driving assembly said loop of wire is contracted in cutting fashion.

8. An apparatus as recited in claim 1 wherein said driving assembly includes means for rotating said cannula while said cannula is being driven forward of said stylet.

9. An apparatus as recited in claim 1 wherein said stylet includes a convergently tapering front end section which slopes inwardly at an angle of 20 to 60 to the horizontal, and the open front end of said cannula including a convergently tapering front end section which slopes inwardly at a common angle.

10. An apparatus as recited in claim 9 wherein the slope of the tapering front end section of said cannula is essentially equal to the slope of the tapering front end section of said stylet.

11. An apparatus as recited in claim 1 wherein the interior surface of said cannula is cylindrical in shape with a maximum diameter of 7 to 15 mm.

12. An apparatus for removing suspect breast tissue, comprising:
    a tapered penetrating member for penetrating the breast tissue;
    a first cutting device for cutting the breast tissue, said first cutting device being adapted to slide and rotate with respect to said penetrating device, said cutting device including a front end defining a tissue receiving cavity;
    a driving assembly for driving said first cutting device past a forward end of said penetrating member such that said tissue receiving cavity is forward of said penetrating member;
    a housing for supporting said driving assembly;
    a second cutting device for cutting breast tissue, said second cutting device being positioned with respect to said first cutting device so as to be adapted to implement a cut essentially transverse to the direction of sliding of said first cutting device such that a removable plug of breast tissue is formed;
    a stand for supporting the housing; and
    a positioning system for placing the forward tapered end of said penetrating member in a predetermined position.

13. An apparatus as recited in claim 12 wherein said driving assembly includes means for rotating said first cutting device while said first cutting device is being driven forward.

14. An apparatus as recited in claim 13 wherein said driving assembly includes a torsion member and a driving member secured to said torsion member and in driving engagement with said first cutting device.

15. An apparatus as recited in claim 14 wherein said driving assembly further includes a cam member in camming engagement with said first cutting device.

16. An apparatus as recited in claim 15 wherein said second cutting device includes a wire arranged in a loop at the forward end of said first cutting device, said wire being secured to said first cutting device at one end and having a portion being engaged with said first cutting device such that upon rotation of said first cutting device the loop of wire is contracted in cutting fashion.

17. An apparatus as recited in claim 12 wherein said second cutting device includes a loop of wire retained in a recess formed at the forward end of said first cutting device.

18. An apparatus as recited in claim 12 wherein said penetrating member is a stylet having a tapered front end and an opening adapted to receive a localization guide wire, and said first cutting device is a cannula which partially surrounds said stylet and is in sliding engagement therewith.

19. An apparatus as recited in claim 12 further comprising activation means for activating said driving assembly by releasing stored potential energy in said driving means.

20. An apparatus as recited in claim 12 wherein said positioning system includes means for stereotopic imaging.

21. A method for removing suspect breast tissue comprising,
positioning a penetrating member with tapered front end such that the tapered front end is at a position behind a suspect breast tissue region;
rotating and driving a cannula so as to rotate and drive the cannula forward of a forward end of said penetrating member and forward of the suspect breast tissue region, rotating and driving said cannula further resulting in activation of cutting means when said cannula is forward of the suspect breast tissue region such that a removable cut-out core of breast tissue is formed.

* * * * *